US011849958B2

(12) United States Patent
Carpentier et al.

(10) Patent No.: US 11,849,958 B2
(45) Date of Patent: Dec. 26, 2023

(54) SURGICAL KIT FOR USE IN A CRANIECTOMY PROCEDURE

(71) Applicants: ASSISTANCE PUBLIQUE HOPITAUX DE PARIS, Paris (FR); SORBONNE UNIVERSITE, Paris (FR); CARTHERA, Paris (FR)

(72) Inventors: Alexandre Carpentier, Paris (FR); Alexandre Vignot, Lyons (FR); Matthieu Cholvy, Peage de Roussillon (FR)

(73) Assignees: ASSISTANCE PUBLIQUE HOPITAUX DE PARIS, Paris (FR); SORBONNE UNIVERSITE, Paris (FR); CARTHERA, Paris (FR)

( * ) Notice: Subject to any disclaimer, the term of this patent is extended or adjusted under 35 U.S.C. 154(b) by 741 days.

(21) Appl. No.: 16/979,999

(22) PCT Filed: Mar. 13, 2019

(86) PCT No.: PCT/EP2019/056246
§ 371 (c)(1),
(2) Date: Sep. 11, 2020

(87) PCT Pub. No.: WO2019/175214
PCT Pub. Date: Sep. 19, 2019

(65) Prior Publication Data
US 2021/0007756 A1    Jan. 14, 2021

(30) Foreign Application Priority Data

Mar. 14, 2018  (FR) ...................................... 1852178

(51) Int. Cl.
*A61B 90/10*   (2016.01)
*A61B 17/17*   (2006.01)
(Continued)

(52) U.S. Cl.
CPC ........ *A61B 17/1739* (2013.01); *A61B 8/4477* (2013.01); *A61B 34/20* (2016.02);
(Continued)

(58) Field of Classification Search
CPC .............. A61B 90/10; A61B 2090/101; A61B 2090/103; A61B 8/4477
See application file for complete search history.

(56) References Cited

U.S. PATENT DOCUMENTS 5,230,338 A    7/1993  Allen et al.
6,932,842 B1   8/2005  Litschko et al.
(Continued)

FOREIGN PATENT DOCUMENTS

CH    711264 A2    12/2016
EP    1047362 A1   11/2000
(Continued)

*Primary Examiner* — Nicholas W Woodall
(74) *Attorney, Agent, or Firm* — BCF LLP

(57) ABSTRACT

The present invention relates to a surgical kit for use in a craniectomy procedure, the surgical kit comprising: a medical device to be implanted in a cranial bone of a patient, the medical device (10) including several transducers for emitting ultrasound waves for treatment of brain tissue, a surgical accessory (20) intended to be positioned on the cranial bone of the patient, the surgical accessory (20) including a body whose outer perimeter defines the dimensions of an opening that is to be made in the cranial bone of the patient in order to receive the medical device, characterized in that the surgical accessory (20) comprises a plurality of holes (201) formed in the body, the position of each hole (201) on the body coinciding with the position of the axis of symmetry of a respective transducer, such that the accessory is able to be positioned optimally through the joint use of a neuronavigation system.

12 Claims, 3 Drawing Sheets

(51) Int. Cl.
    *A61B 34/20*  (2016.01)
    *A61N 7/00*   (2006.01)
    *A61B 8/00*   (2006.01)
(52) U.S. Cl.
    CPC ............... *A61B 90/10* (2016.02); *A61N 7/00* (2013.01); *A61B 2090/103* (2016.02); *A61N 2007/0026* (2013.01)

(56) References Cited

U.S. PATENT DOCUMENTS

| | | | |
|---|---|---|---|
| 7,479,146 | B2 | 1/2009 | Malinowski |
| 7,651,506 | B2 | 1/2010 | Bova et al. |
| 8,936,601 | B2 | 1/2015 | Carignan et al. |
| 8,974,535 | B2 | 3/2015 | Antonyshyn et al. |
| 9,044,195 | B2 | 6/2015 | Manwaring et al. |
| 9,061,133 | B2 * | 6/2015 | Wurster ............... A61B 8/4227 |
| 9,289,270 | B2 * | 3/2016 | Gielen ................. A61B 90/18 |
| 9,504,402 | B2 | 11/2016 | Wahlstrand |
| 9,707,049 | B1 * | 7/2017 | Allen .................. A61B 90/14 |
| 9,744,042 | B2 | 8/2017 | Beerens et al. |
| 11,058,541 | B2 * | 7/2021 | Gordon ................ A61F 2/2875 |
| 2002/0052610 | A1 | 5/2002 | Skakoon et al. |
| 2004/0102778 | A1 | 5/2004 | Huebner et al. |
| 2006/0189989 | A1 * | 8/2006 | Bert ................... A61B 17/1728 606/281 |
| 2007/0129652 | A1 | 6/2007 | Nita |
| 2007/0225773 | A1 | 9/2007 | Shen et al. |
| 2008/0004676 | A1 | 1/2008 | Osypka et al. |
| 2009/0112278 | A1 | 4/2009 | Wingeier et al. |
| 2009/0112280 | A1 | 4/2009 | Wingeier et al. |
| 2012/0078140 | A1 | 3/2012 | Nita |
| 2012/0179147 | A1 | 7/2012 | Geebelen et al. |
| 2013/0345599 | A1 | 12/2013 | Lin et al. |
| 2014/0277019 | A1 | 9/2014 | Pearson |
| 2015/0196369 | A1 | 7/2015 | Glossop |
| 2015/0265448 | A1 | 9/2015 | Haberl et al. |
| 2017/0172585 | A1 | 6/2017 | Pfeiffer |
| 2017/0273794 | A1 | 9/2017 | Howard et al. |
| 2021/0299439 | A1 * | 9/2021 | Shamir ................ G16H 30/40 |

FOREIGN PATENT DOCUMENTS

| | | |
|---|---|---|
| EP | 2515750 A2 | 10/2012 |
| EP | 2539021 A2 | 1/2013 |
| WO | 2009/115283 A1 | 9/2009 |
| WO | 2009/132389 A1 | 11/2009 |
| WO | 2011/101039 A1 | 8/2011 |
| WO | 2017/001911 A1 | 1/2017 |

* cited by examiner

SURGICAL KIT FOR USE IN A CRANIECTOMY PROCEDURE

CROSS-REFERENCE TO RELATED APPLICATIONS

This application is a national phase filing under 35 U.S.C. § 371 of International Application No. PCT/EP2019/056246 filed on Mar. 13, 2019, which claims benefit of priority from French Patent Application No. 1852178 filed Mar. 14, 2018, the contents of which are hereby incorporated by reference in their entirety.

FIELD OF THE INVENTION

The present invention relates to the general technical field of the methods for treating a human or animal brain tissue by ultrasound in order to assist a practitioner in the treatment of a pathology.

More specifically, the present invention relates to a surgical accessory useful to the practitioner during the implantation of a medical device in the cranial bone of a patient.

BACKGROUND OF THE INVENTION

Different techniques are known for treating a brain tissue.

In particular, a known technique consists in using an intracranial device as illustrated in FIG. 1. This intracranial device 10 comprises:
- a support structure 100,
- a plurality of transducers 101-109 fixed on the support structure 100 for the generation of ultrasound waves for treating a brain disease,
- an electrical connection terminal 110 mounted on the support structure 100 for the attachment of the intracranial implant to an outer electric power supply source.

Prior to the treatment of the patient, it is necessary to implant the intracranial device in the patient's skull. To do so, the practitioner performs a craniectomy. An incision is made in the scalp, then the skin (and the muscles if need be) is/are lifted to expose the skull. Burr holes are made in the skull in the appropriate locations, and a surgical saw (craniotome) is used to cut out a bone flap by travelling from one burr hole to another. A removable cranial bone flap is thus obtained, leaving room for a cranial opening in which the intracranial device can be positioned. The intracranial device is fixed, by appropriate fixing means on the bone to the periphery of the opening, then the scalp and the muscles are put back in place to cover the intracranial device.

In order for the cranial opening to be minimal, and for the dura mater to be protected by the device, it is desirable that the dimensions of the opening correspond to the minimum dimensions necessary for the adjustment of the intracranial device.

Thus, it is necessary to trace the contours of the opening to be made on the patient's skull before making the cutouts allowing the removal of the bone flap.

Furthermore, for good effectiveness of the therapeutic treatment, the intracranial device—and therefore the opening made in the patient's skull—must be positioned accurately relative to the brain tissue to be treated. The use of the intraoperative neuro-navigation apparatuses allows optimizing the positioning of the bone opening relative to the location of the underlying lesion to be treated.

An aim of the present invention is to propose a surgical kit enabling optimal dimensioning and correct positioning of an opening in a cranial bone of a patient, particularly for the implantation of an intraosseous device.

BRIEF DESCRIPTION OF THE INVENTION

To this end, the invention proposes a surgical kit for use during a craniectomy procedure, the surgical kit comprising:
- a medical device to be implanted in a cranial bone of a patient, the medical device including a support structure and several transducers mounted on the support structure for the emission of ultrasound waves for treating a brain tissue,
- a surgical accessory intended to be positioned on the cranial bone of the patient, the surgical accessory including a body dimensioned to approximate the dimensions of the support structure of the medical device, the outer perimeter of the body defining the dimensions of an opening to be made in the cranial bone of the patient in order to receive the medical device, remarkable in that the surgical accessory comprises a plurality of holes arranged in the body, the position of each hole on the body coinciding with the position of the axis of symmetry of a respective transducer on the support structure (each hole defining a marker for the end of a neuronavigation system in order to facilitate optimal positioning (in particular relative to characteristics of the lesion to be treated such as its shape and/or its position) of the opening to be made in the cranial bone).

Preferred but non-limiting aspects of the present invention are as follows:
- the body may advantageously comprise a central lumen, the surgical accessory comprising at least one pair of opposite tabs, in particular two pairs of opposite tabs, each tab protruding from the body inwardly of the central lumen;
- the central lumen can be X-shaped;
- the body may have a substantially parallelepiped shape with rounded corners, for example square shape with rounded corners, the rounding of each corner having a radius of curvature substantially equal to half the diameter of a medical drill bit (craniotome) used when making the opening in the cranial bone of the patient;
- the body may have a substantially parallelepiped shape, for example square shape, the surgical accessory comprising four notches in the form of an arc of a circle disposed facing a respective corner of the body;
- the concavity of each notch can be oriented towards its associated corner, the radius of curvature of each notch being substantially equal to half the diameter of a medical drill bit used when making the opening in the cranial bone of the patient;
- the body can be made in a deformable or semi-rigid material;
- the body can be made of medical grade silicone;
- the lower face of the body intended to come into contact with the cranial bone of the patient and/or the upper face opposite the lower face can be textured;
- the surgical kit may further comprise at least one strut able to be positioned between the medical device and the cranial bone of the patient;
- each strut may comprise a peripheral frame including through-orifices for the passage of screws for fixing the medical device on the cranial bone of the patient;

each strut may further comprise lugs protruding outwardly of the peripheral frame.

BRIEF DESCRIPTION OF THE DRAWINGS

Other advantages and characteristics of the surgical kit will emerge better from the following description of several alternative embodiments, given by way of non-limiting examples, from the appended drawings in which.

DETAILED DESCRIPTION OF THE INVENTION

Figure 1:
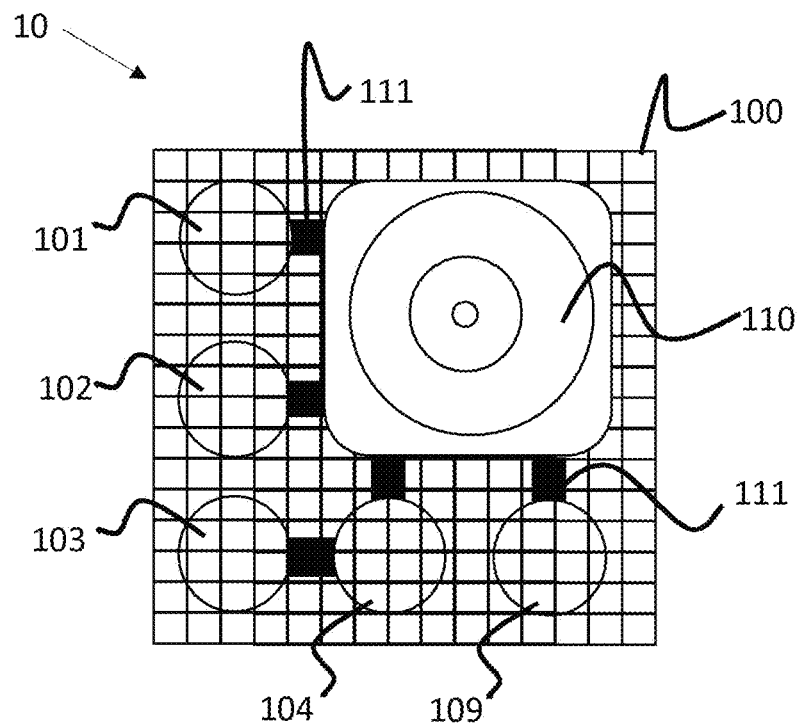
FIG. 1 is a top view schematic representation of an intracranial device.

An example of a surgical kit according to the invention will now be described in more detail with reference to the figures. In these various figures, the equivalent elements are designated by the same reference numeral.

The surgical kit comprises a medical device 10 to be implanted into a cranial bone of a patient, and a surgical accessory 20 intended to be positioned on the cranial bone of the patient.

The surgical accessory 20 allows facilitating the positioning of an opening in the cranial bone of the patient and delimiting the contours thereof for the implantation of the medical device 10. Even if the shapes of the surgical accessory 20 and of the medical device 10 are not identical, the shape of the surgical accessory 20 depends on the shape of the medical device 10. The same applies to its dimensions. Particularly, the outer perimeter of the surgical accessory 20 defines the shape and the dimensions of the opening into which the medical device 10 is intended to be inserted.

In the following, an alternative embodiment of the invention will be described with reference to a surgical kit in which the medical device 10 and the surgical accessory 20 have a substantially square shape, it being understood by those skilled in the art that the elements of this kit can have other shapes (rectangular, triangular, any parallelepiped shape, etc.).

1. Medical Device

Figure 2:
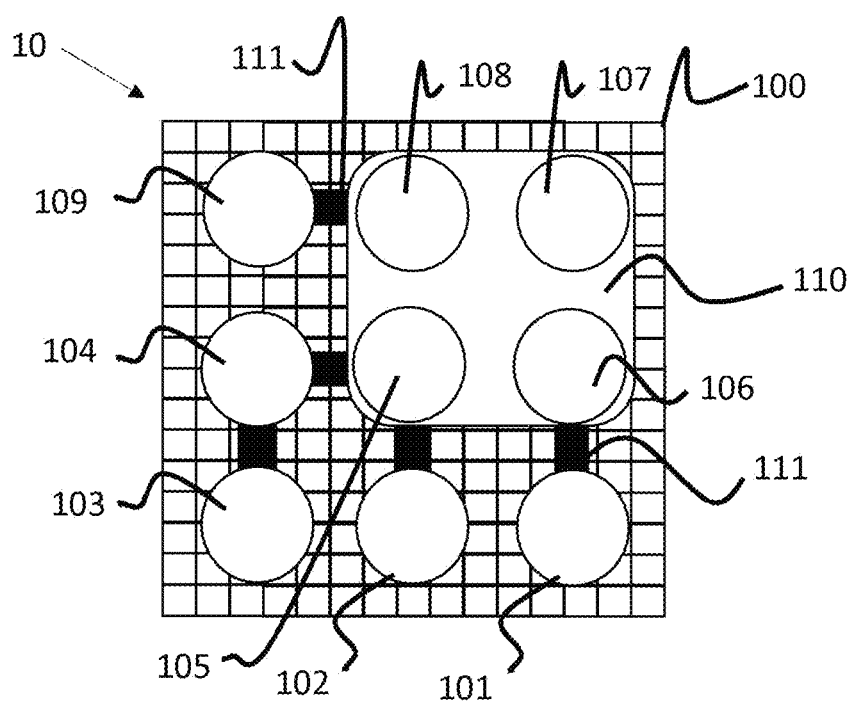
FIG. 2 is a bottom view schematic representation of the intracranial device.

Referring to FIGS. 1 and 2, the medical device 10 comprises:
- a support structure 100,
- transducers 101-109 fixed on the support structure 100 for the generation of ultrasound waves for treating a brain tissue,
- an electrical connection terminal 110 mounted on the support structure 100 for the attachment of the medical device to an outer control unit.

The support structure 100 can consist of a grid made of titanium. It has a square shape and may extend substantially in a plane or have a convexity to follow the curvature of the cranial bone of the patient. The support structure 100 is intended to be fixed in the cranial bone of the patient at its peripheral edge thanks to anchoring screws or to any other fixing means known to those skilled in the art.

In the embodiment illustrated in FIG. 1, the medical device 10 comprises nine circular transducers 101-109 of 10 millimeters in diameter each. These nine transducers 101-109 are also distributed over the support structure 100 to form a transducer array, the centers of two adjacent transducers being spaced by a distance of 20 millimeters. They are intended to come into contact with the outer surface of the dura mater. The transducers 101-109 are connected together via electrical connection elements 111—such as flex-rigid printed circuit boards—to allow the sequential supply of the transducers 101-109 with electrical energy and the transfer of electrical activation signals derived from the outer control unit (not represented).

The electrical connection terminal 110 allows connecting the medical device 10 (once it is implanted) to the outer control unit which supplies the transducers 101-109 with electrical energy, and sets their operating parameters. Such a connection terminal 110 is in particular known from document EP 2 539 021 and will not be described in more detail below. It is adapted to cooperate with connection means including:
- an electric cable, one end of which is connected to the control unit, and
- a transdermal needle attached to the other end of the cable.

Figure 3:
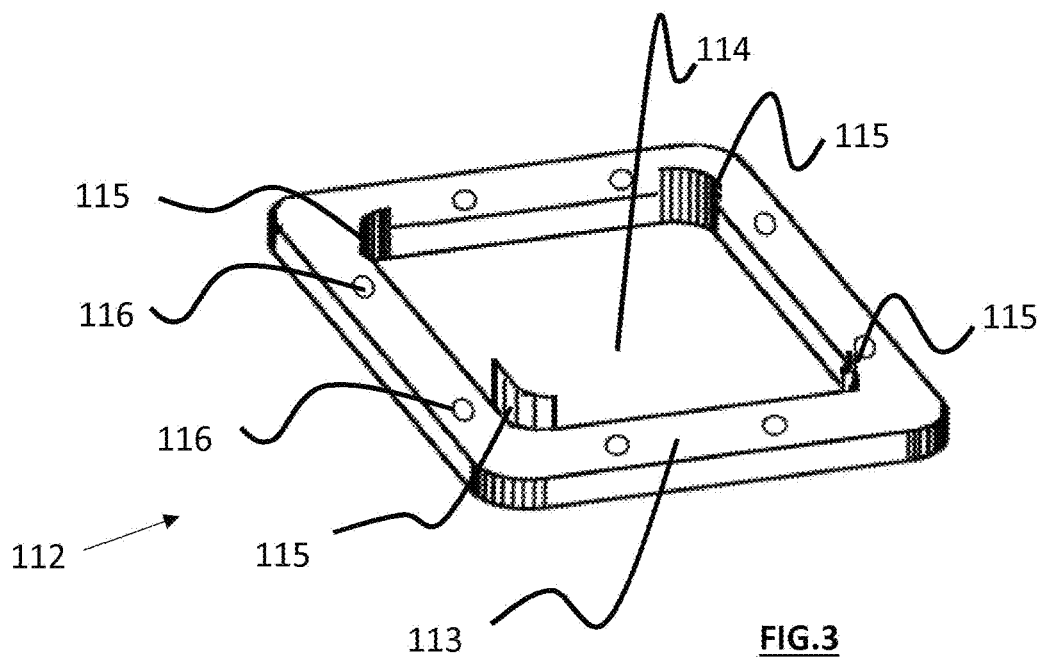
FIG. 3 is a perspective representation of a strut.

Referring to FIG. 3, the medical device 10 may also comprise one (or several) strut(s) 112. In particular, the medical device 10 may comprise two struts 112 of 1 millimeter thick and a strut 112 of 2 millimeters thick. This (or these) strut(s) allow(s) adapting the height of positioning of the support structure 100 according to the thickness of the cranial bone of the patient. These struts 112 can also be used to tilt the support structure 100 on the cranial bone in order to orient the transducers 101-109 towards the brain tissue to be treated, for example by cutting out a portion of a strut and assembling it to another strut in order to form a resulting strut of variable thickness. Each strut 112 comprises a peripheral frame 113 intended to be positioned between the support structure 100 and the cranial bone. The dimensions of the central opening 114 of each strut 112 are slightly larger than the dimensions of the surface occupied by the transducers 101-109 fixed on the support structure 100 to allow their passage through the central opening 114.

Advantageously, the peripheral frame 113 of each strut 112 includes through-orifices 116 with a diameter greater than that of the screws for fixing the implant on the bone so that the screwing of the screws does not deform the strut 112 during its passage.

Preferably, each strut 112 also includes positioning lugs 115 intended to match the shape of the cranial opening. These lugs protrude outwardly of the peripheral frame 113; they can be disposed in the angles of the strut (see FIG. 3). These lugs 115 are intended to extend in the opening made in the cranial bone of the patient when the strut 112 is placed on the patient's skull. Thus, the strut remains centered in the opening, without the surgeon having to hold it manually when placing the implant.

The medical device 10 illustrated in FIGS. 1 and 2 is intended to be inserted into a square opening of 58×58 millimeters made by removal of a bone flap from the cranial bone of the patient. To facilitate the positioning and the dimensioning of this opening, the practitioner can use the surgical accessory 20 illustrated in FIG. 4.

2. Chirurgical Accessory

Figure 4:
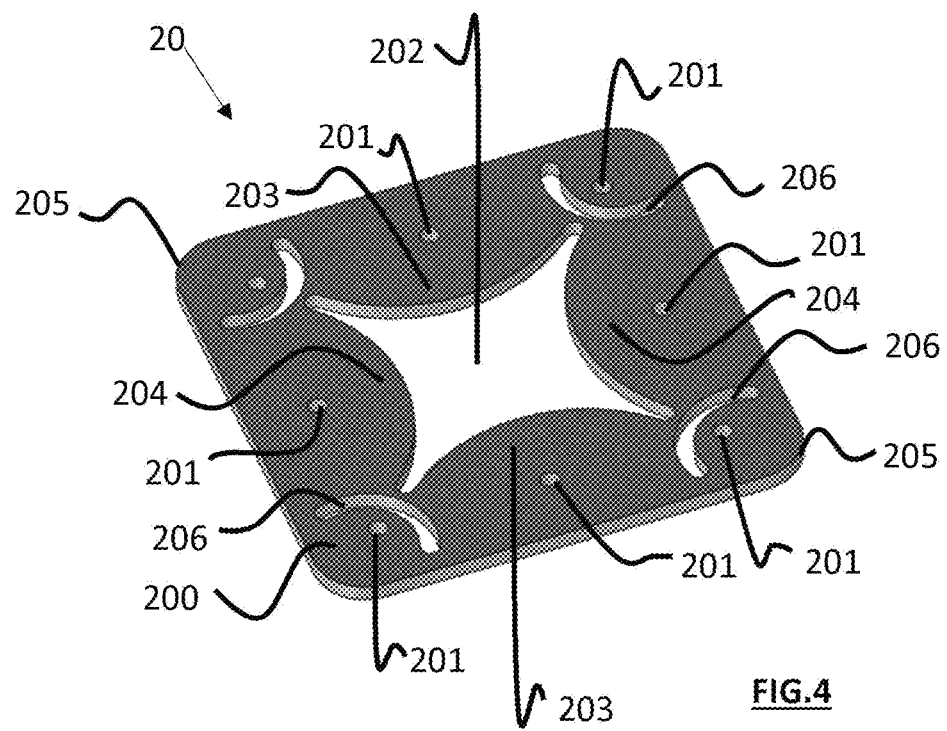
FIG. 4 is a perspective representation of a surgical accessory.
Figure 5:
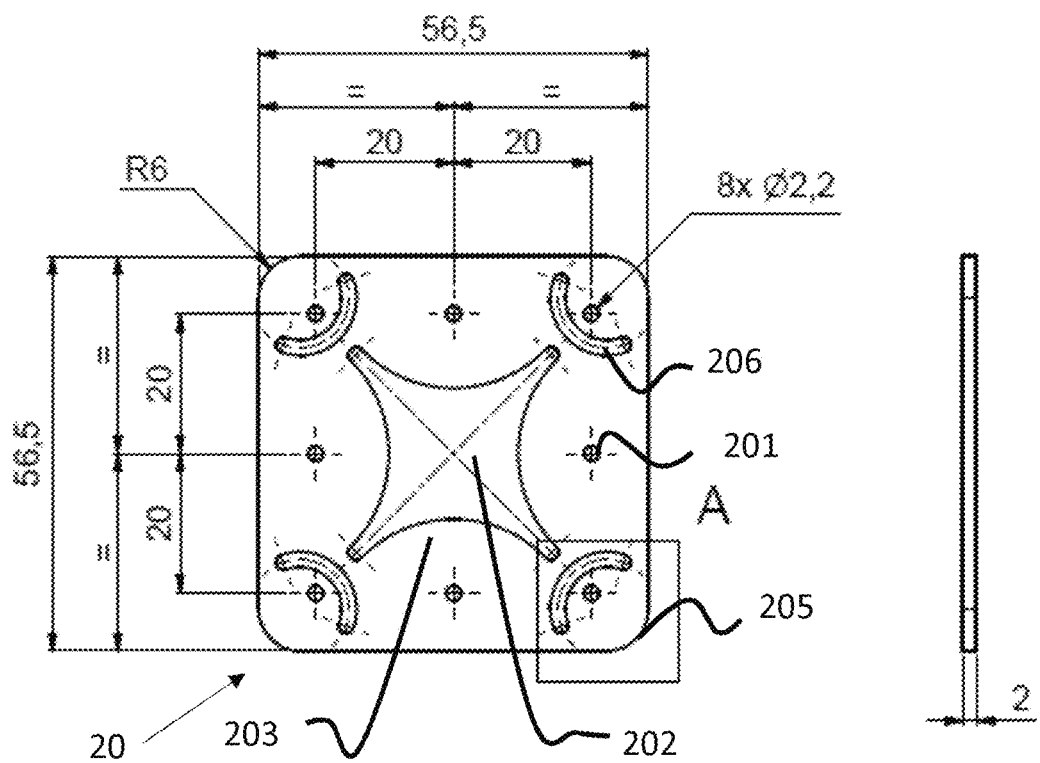
FIGS. 5 and 6 are top view schematic representations of the surgical accessory.

Referring to FIGS. 4 and 5, the surgical accessory 20 comprises a body 200 dimensioned to approximate the dimensions of the support structure 100 of the medical device 10. The body 200 is substantially planar. Its outer perimeter defines the dimensions of the opening to be made in the cranial bone of the patient in order to receive the medical device 10. In the embodiment illustrated in FIG. 4, the outer perimeter of the body 200 has a substantially square shape. Preferably, the body 200 is made in an elastically deformable material, such as medical grade silicone. The face(s) of the body 200 can be textured in order to ensure limiting the risks of slipping:
- the surgical accessory on the patient's skull and/or
- the practitioner's fingers on the surgical accessory.

Figure 6:
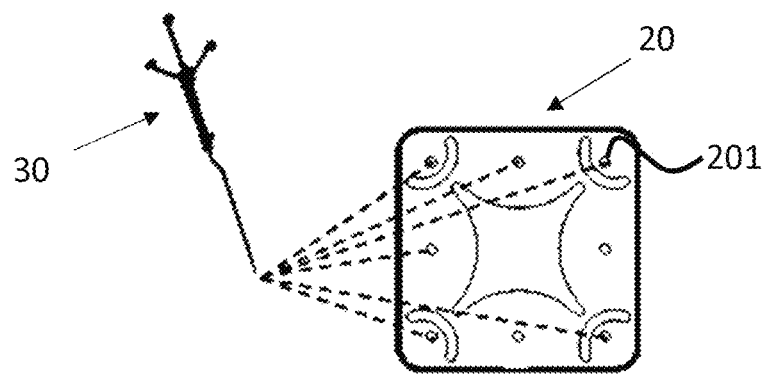

Advantageously, the body 200 of the surgical accessory 20 comprises a plurality of holes 201. The position of each of these holes 201 coincides with the position of the axis of symmetry of a respective transducer 101-109 on the support structure 100 of the medical device. 10. Thus, placing the surgical accessory on the patient's skull allows the practitioner to visualize the positions that the transducers 101-109 will have once the medical device 10 is implanted. The presence of these holes 201 allows the practitioner using the surgical accessory 20 to accurately define an ideal positioning for the opening to be made relative to the position of the brain tissue to be treated. To this end, the practitioner can use a neuro-navigation pointer 30 known to those skilled in the art: the positioning of this pointer 30 at each hole 201 allows him to check (on display means) whether the position of the surgical accessory 20 on the patient's skull corresponds with a desired position for the medical device 10 in order to ensure effective treatment of the brain tissue to be treated (cf. FIG. 6).

The holes 201 can be of different shapes, for example circular or oblong shape. In some alternative embodiments, all the holes 201 arranged in the body 200 are of identical shape. However, in other alternative embodiments, the (or some of the) holes 201 disposed on the body 200 can be of different shapes. This allows differentiating the different transducers 101-109. Providing this additional information to the practitioner allows facilitating the orientation of the medical device.

The surgical accessory 20 also comprises a central lumen 202 arranged in the center of the body 200. This central lumen 202 allows facilitating the deformation of the surgical accessory 20 when it is placed on the patient's skull. This allows ensuring the conformation of the surgical accessory 20 to the curvature of the patient's skull. The central lumen 202 can have different shapes. In the embodiment illustrated in FIG. 4, the central lumen is X-shaped to increase the flexibility of the body 200.

To facilitate the pressing of the body 200 on the patient's skull, the surgical accessory 20 also comprises one (or several) pair(s) of opposite tabs 203, 204 extending inwardly of the central lumen 202. By applying his fingers on the tabs, the practitioner can hold the surgical accessory 20 in position during the phases of determining an optimal position for the opening and of tracing the latter on the patient's skull. In the embodiment illustrated in FIG. 4, the surgical accessory 20 comprises two pairs 203, 204 of opposite tabs, each tab extending inwardly of the central lumen.

The corners 205 of the body 200 may be rounded. In this case, the radius of curvature of the rounding of each corner 205 is chosen to be substantially equal to half the diameter of a medical drill bit used when making the opening in the cranial bone of the patient. Thus, following the tracing, the practitioner has a marker on the patient's skull for facilitating the positioning of the medical drill bit.

To further facilitate the positioning of the medical drill bit, the surgical accessory 20 may comprise four notches 206 in the form of an arc of a circle disposed facing a respective corner 205 of the body 200. Here again, the radius of curvature of the notches 206 is chosen to be substantially equal to half the diameter of a medical drill bit. Each notch 206 thus formed, whose concavity is oriented towards its associated corner, the center of the notches 206, corresponding to the center of the corners 205, constitutes a positioning marker for the medical drill bit for boring the burr hole.

3. Operating Principle

The operating principle of the surgical kit described above is as follows.

The practitioner makes an incision in the patient's scalp. The skin and the muscles are lifted to expose the skull.

Once the patient's skull is exposed, the practitioner presses the surgical accessory 20 on the patient's skull in an area previously defined to receive the medical device. To do so, the practitioner positions his fingers at the pairs of tabs 203, 204 and applies a force tending to press the body of the accessory against the patient's skull.

The practitioner inserts the neuro-navigation pointer 30 into the holes 201 of the accessory 20. The position and the orientation of the neuro-navigation pointer (measured by a neuro-navigation system known to those skilled in the art) are reported in a previously acquired three-dimensional image (for example using a magnetic resonance imaging technique) illustrating the skull and the brain tissue to be treated.

The resulting image thus obtained is displayed on display means to allow the practitioner to verify the position and the orientation of the surgical accessory 20.

Once the surgical accessory 20 is disposed in a desired position and orientation, the practitioner draws—by using a medical pen—the contour of the body 200 on the patient's skull. He also traces the notches 206 on the patient's skull.

The practitioner then removes the surgical accessory 20 to carry out the cutting of a bone flap.

The practitioner successively positions the medical drill bit at the various areas delimited by the rounded corners 205 and the notches 206. Holes are drilled in the skull (for example, 2, 3 or 4 holes according to the needs of the practitioner).

The practitioner then uses a surgical saw (craniotome) to cut out the skull at the straight segments drawn thereon and corresponding to the contour of the opening.

Once the cutouts are made, the bone flap is extracted from the skull: the opening in which the medical device must be positioned is thus obtained.

The practitioner installs the medical device 10 in the opening and fixes it on the contour of the opening.

Once the medical device is fixed, the practitioner puts the scalp and the muscles back in place to cover the medical device 10.

The reader will understand that many changes can be made to the invention described above without physically departing from the new teachings and advantages described here.

Therefore, all such modifications are intended to be incorporated within the scope of the appended claims.

The invention claimed is:

1. A surgical kit for use during a craniectomy procedure, the surgical kit comprising:
- a medical device capable of being implant in a cranial bone of a patient, the medical device including a support structure and several transducers mounted on the support structure for the emission of ultrasound waves for treating a brain tissue,
- a surgical accessory capable of being positioned on the cranial bone of the patient, the surgical accessory including a body dimensioned to approximate the dimensions of the support structure of the medical device, the outer perimeter of the body defines dimensions of an opening capable of being made in the cranial bone of the patient in order to receive the medical device, wherein the surgical accessory comprises a plurality of holes arranged in the body, the position of each hole on the body coinciding with the position of the axis of symmetry of a respective transducer on the support structure, each hole defining a marker for the end of a neuronavigation system in order to facilitate optimal positioning of the opening to be made in the cranial bone.

2. The surgical kit according to claim 1, wherein the body comprises a central lumen, the surgical accessory comprising at least one pair of opposite tabs, in particular two pairs of opposite tabs, each tab protruding from the body inwardly of the central lumen.

3. The surgical kit according to claim 2, wherein the central lumen is X-shaped.

4. The surgical kit according to claim 1, wherein the body has a substantially parallelepiped shape with rounded corners, the rounding of each corner having a radius of curvature capable of being substantially equal to half a diameter of a medical drill bit used to make the opening in the cranial bone of the patient.

5. The surgical kit according to claim 1, wherein the body has a substantially parallelepiped shape, the surgical accessory comprising four notches in the form of an arc of a circle disposed facing a respective corner of the body.

6. The surgical kit according to claim 5, wherein the concavity of each notch is oriented towards its associated corner, the radius of curvature of each notch capable of being substantially equal to half the diameter of a medical drill bit used to make the opening in the cranial bone of the patient.

7. The surgical kit according to claim 1, wherein the body is made in a deformable or semi-rigid material.

8. The surgical kit according to claim 7, wherein the body is made of medical grade silicone.

9. The surgical kit according to claim 1, wherein a lower face of the body is capable of contacting the cranial bone of the patient and/or an upper face opposite the lower face is textured.

10. The surgical kit according to claim 1, which further comprises at least one strut able to be positioned between the medical device and the cranial bone of the patient.

11. The surgical kit according to claim 10, wherein each strut comprises a peripheral frame including through-orifices for the passage of screws for fixing the medical device on the cranial bone of the patient.

12. The surgical kit according to claim 10, wherein each strut further comprises lugs protruding outwardly of the peripheral frame.

* * * * *